United States Patent [19]

Krämer et al.

[11] Patent Number: 4,511,694

[45] Date of Patent: Apr. 16, 1985

[54] HYDROPHILIC POLYMER CARRIER FOR PROTEINS

[75] Inventors: Dieter Krämer, Mainz; Horst Pennewiss, Darmstadt-Neu-Kranichstein; Hermann Plainer, Reinheim; Reiner Schnee, Darmstadt-Arheilgen; Waldemar Schleier, Darmstadt, all of Fed. Rep. of Germany

[73] Assignee: Röhm GmbH, Darmstadt, Fed. Rep. of Germany

[21] Appl. No.: 344,524

[22] Filed: Feb. 1, 1982

[30] Foreign Application Priority Data

Feb. 21, 1981 [DE] Fed. Rep. of Germany ....... 3106456

[51] Int. Cl.$^3$ .......................... C08F 2/06; C08F 2/10; C08F 2/14
[52] U.S. Cl. ................................... 525/54.1; 526/210; 526/212; 526/227; 526/273
[58] Field of Search ............... 525/54.1; 526/273, 210, 526/212, 227

[56] References Cited

U.S. PATENT DOCUMENTS

3,948,866 4/1976 Pennewiss et al. ................ 260/79.3
4,070,348 1/1978 Krämer et al. ..................... 525/54.1
4,190,713 2/1980 Krämer et al. ..................... 525/54.1

FOREIGN PATENT DOCUMENTS

2009218 9/1971 Fed. Rep. of Germany .
2237316 2/1974 Fed. Rep. of Germany .
2722751 11/1978 Fed. Rep. of Germany .
2442248 6/1980 France .

OTHER PUBLICATIONS

Brandrup–Immergut, "Polymer Handbook", pp. IV–337, IV–340, IV–341, IV–348, IV–349, (1975).

*Primary Examiner*—Allan M. Lieberman
*Attorney, Agent, or Firm*—Curtis, Morris & Safford

[57] ABSTRACT

What are disclosed are a method for making a pearl-like crosslinked hydrophilic carrier polymer, capable of binding proteins, by the inverse pearl polymerization of a monomer phase comprising a monomer mixture of a certain composition and a diluent therefor, also of a certain composition, said diluent comprising at least two components which can be chosen in nature and amount to optimize the protein binding capacity of the polymer, and pearl-like hydrophilic carrier polymers made by this method.

7 Claims, No Drawings

HYDROPHILIC POLYMER CARRIER FOR PROTEINS

The present invention relates to a method for preparing pearl-like hydrophilic carrier polymers capable of binding proteins, to such polymers, and to their uses.

It is known from German Auslegeschrift No. 22 37 316 to prepare pearl-like crosslinked copolymers, swellable in water, by an inverse pearl polymerization of a monomer mixture comprising monomers which are capable of bonding proteins, a crosslinking monomer, and a monomer which is hydrophilic. In order to achieve good swellability and an extensively crosslinked network, the monomer mixture is dissolved in a solvent which is immiscible with the non-polar organic polymerization medium, the solution is suspended in the form of droplets in this medium, and is polymerized in this form. Formamide, dimethylformamide, or dimethylsulfoxide are used as solvents for the monomer mixture, for example.

According to German Offenlegungsschrift No. 27 22 751, the binding activity of the hydrophilic pearl polymers prepared in this way is increased still more if the portion of the crosslinking monomers in the monomer mixture is 5 weight percent or more and the weight fraction of acrylamide or methacrylamide or of methylene-bis-acrylamide or methylene-bis-methacrylamide exceeds certain limiting values. Using this method, polymers having a hollow pearl structure, which is considered essential for a high binding activity, are formed.

The known hydrophilic pearl polymers contain monomer units having oxirane groups (epoxy groups) as the groups which are capable of bonding proteins, e.g. glycidyl methacrylate or allyl glycidyl ether. These units permit water soluble proteins to bond covalently to the polymer with retention of their biological activity. Although high binding capacities can be reached in this fashion with a number of enzymes, the binding capacity remains unsatisfactory for certain other enzymes. By "binding capacity" is to be understood that enzymatic activity which can be achieved at maximum loading of pearl polymer with a particular enzyme. It has been determined that the binding capacity cannot be increased, or cannot be essentially increased over an enzyme-specific limit, by increasing the oxirane group content of the pearl polymer or by employing an enzyme solution of higher concentration for loading.

The present invention has as its object increasing the binding capacity of hydrophilic pearl polymers which bond proteins covalently to oxirane groups. In a narrower sense, the object of the invention is to optimize the binding capacity of a pearl-like carrier polymer with respect to whatever protein is to be bound thereto.

It has now been found that pearl polymers having an increased and, in some cases for certain enzymes an optimized, binding capacity are formed according to the method of the present invention. The binding capacity is adjusted according to the present invention by the addition of a special combination of diluents to the monomer mixture.

Water, formamide, glycol, or dimethylsulfoxide, or mixtures thereof can be used as component (A) of the diluent. Surprisingly, the binding capability for proteins can be maintained even when water is used, although water reacts readily with the epoxide groups necessary for protein bonding.

As component (B) of the diluent, organic liquids of medium to high polarity, resulting from the presence of oxygen atoms, have proved suitable. A sufficient polarity is present if the content of oxygen is at least 20 percent by weight and the molecular weight is below 200. Aliphatic organic liquids which contain oxygen in form of carbonyl groups or hydroxyl groups are preferred. On the other hand, carboxyl groups are less preferred because of their high reactivity with oxirane groups. Oxygen atoms found in ether-like linkages also contribute to the desired polarity and are found, for example, in aliphatic or cycloaliphatic ethers and in aliphatic esters. The components (B) suitable for the method of the invention are predominantly characterized by a total solubility parameter, $\delta$, from 9 to 15 and preferably from 11 to 14.5 Hildebrand-units, or by a dispersive solubility parameter, $\delta_D$, in the region from 7 to 9, preferably from 7.4 to 8.5 Hildebrand units (cf. Polymer-Handbook Second Edition, 1975, pages IV 337 et seq., incorporated herein by reference).

The following list contains Examples of diluent components (B) and their characteristic values:

|  | Molecular Weight | Oxygen Content (% by weight) | Solubility parameters | |
| --- | --- | --- | --- | --- |
|  |  |  | $\delta$ | $\delta_D$ |
| Methanol | 32 | 50.0 | 14.3 | 7.4 |
| Ethanol | 46 | 35.0 | 12.9 | 7.7 |
| n-Propanol | 60 | 26.7 | 11.9 | 7.8 |
| i-Propanol | 60 | 26.7 | 11.5 | — |
| n-Butanol | 74 | 21.6 | 11.3 | 7.8 |
| Acetone | 58 | 27.6 | 9.8 | 7.6 |
| Diacetone alcohol | 116 | 27.6 | 10.2 | 7.7 |
| Methylethyl ketone | 72 | 22.2 | 9.3 | 7.8 |
| Tetrahydrofuran | 72 | 22.2 | 9.5 | 8.2 |
| Dimethylformamide | 73 | 22.0 | 12.1 | 8.5 |
| Ethyl acetate | 88 | 36.4 | 9.1 | 7.4 |
| Ethylene glycol | 90 | 35.5 | 8.3 | — |
| Diethylene glycol | 118 | 27.1 | 11.9 | 7.9 |

The mixture of the monomers and the diluent components (A) and (B) must form a homogeneous phase, if possible already at room temperature (20° C.), which is not the case for all conceivable combinations. Further, this mixture must be incompatible with the organic medium in which it is suspended, at least at the polymerization temperature, so that a separate suspended monomer phase forms. If the diluent components have a certain solubility in the organic medium, the monomer phase can be depleted of these components, which can lead to an alteration in the binding capacity. In order nevertheless to be able to reach a particular binding capacity, it is recommended that the organic medium be priorly saturated with the diluent components (A) or (B) soluble therein or adjusted to the corresponding equilibrium concentrations. In this way, the polarity of the organic medium is increased. The addition of the diluent components to the organic medium must remain under that limit at which the monomer phase would dissolve in the organic medium.

By the choice of a sufficiently non-polar organic medium, an approach to this limit can be avoided. Aliphatic hydrocarbons and chlorohydrocarbons, and mixtures thereof, are preferred.

It is advantageous if the components (A) and (B) are completely miscible with each other, if possible already at room temperature. A preferred group of the organic liquids of component (B) are those liquids which are completely miscible with water at room temperature, such as methanol, ethanol, propanol, acetone, dimethylformamide, or tetrahydrofuran. A particularly advantageous combination, also from a technical viewpoint, is a mixture of methanol and water.

The mixing ratio of components (A) and (B) with each other can be chosen within wide limits, from between about 99:1 and 1:99 parts by weight, wherein the region from 90:10 to 10:90 is preferred. The amount of the diluent, consisting of (A) and (B), in the monomer phase can be between 20 and 90 percent by weight and preferably amounts from 50 to 90 percent by weight. For the determination of this fraction and the ratio of (A) to (B), a series of different pearl polymers are suitably prepared as trial batches and in each case the binding capacity of the batch for a particular protein is determined. In this way, as a rule, it is found that by variation of the ratio (A):(B), there is an increase in the binding capacity up to a maximum value and a decrease thereafter as is shown below, by way of example, for the inverse pearl polymerization of a monomer phase comprising 30 parts by weight of methacrylamide,
30 parts by weight of N,N'-methylene-bis-methacrylamide,
20 parts by weight of glycidyl methacrylate,
20 parts by weight of allyl-glycidyl ether, and
73 parts by weight of a mixture of methanol and formamide, which is used for an optimal binding of penicillin-acylase (PCA):

| Diluent | | Maximum Enzyme activity (U/g) |
|---|---|---|
| A Formamide | B Methanol | |
| 10 | 90 | 71 |
| 30 | 70 | 101 |
| 50 | 50 | 124 |
| 90 | 10 | 125 |
| 100 | 0 | 95 |

For other enzymes, the activity maximum in this system can be at a different ratio of (A):(B).

In order to assure the hydrophilicity of the pearl polymer, the monomer mixture employed in its preparation must predominantly comprise hydrophilic monomers. To this class belong acrylamide, methacrylamide, and their methylene-bis-amides, as well as such unsaturated free radically polymerizable monomers as form at least 10 percent aqueous solutions at room temperature and which preferably contain no ionic groups or groups ionizable by the addition of acid or base. Examples of preferred hydrophilic comonomers are the hydroxyalkyl esters of unsaturated polymerizable carboxylic acids, such as hydroxyethyl acrylate and hydroxyethyl methacrylate, 2-hydroxypropyl-acrylate or 2-hydroxypropyl-methacrylate, and N-vinyl pyrrolidone. Acrylamide or methacrylamide and their methylene-bis-amides are present in an amount of at least 30 percent by weight and preferably at least 50 percent by weight. Further hydrophilic comonomers can optionally be present in an amount up to 65 percent by weight of the polymerizable monomers.

Monomers having oxirane groups are present in the monomer mixture in amounts from 5 to 60 percent by weight. Examples of these monomers are glycidyl acrylate and glycidyl methacrylate and allyl-glycidyl ether, which can also be used together if desired. After reaction of the pearl polymer with a protein and extensive contact with an aqueous medium, the oxirane groups are gradually completely converted into hydroxy groups, whereby the hydrophilicity of the polymer is further increased. Further comonomers which are less hydrophilic and which give saturated aqueous solutions of less than 10 percent at room temperature decrease the hydrophilicity of the polymers and are used, if at all, in amounts of less than 25 percent by weight.

The pearl polymers prepared according to the present invention are strongly crosslinked. The comonomers effective as crosslinking agents and having two or more ethylenically unsaturated polymerizable groups in the molecule make up at least 5 percent by weight of the monomer mixture. Preferably, methylene bis-acrylamide or methylene-bis-methacrylamide serve as the cross-linking agent. In this case, the amount of the crosslinking monomers can exceed 90 percent by weight of the polymerizable monomers. However, if other crosslinking monomers are employed instead of these, or in addition to these, then the amount of such monomers is limited to at most 45 percent by weight.

The suspended monomer phase contains polymerization initiators and optional further auxiliary agents as further components, as is known from the present state of the art.

The method of inverse pearl polymerization is known per se. The monomer phase is suspended with stirring in an organic medium, which preferably contains a dispersing agent soluble therein, to form droplets between about 10 microns and 1000 microns in diameter. The size of the particles can be adjusted to a desired value by a choice of the kind and amount of the dispersing agent and the velocity of stirring. The polymerization takes place within the monomer droplets and converts these into solid pearl polymer which can be separated from the organic medium after conclusion of the polymerization. Advantageous embodiments of this method are described in German Patent No. 20 09 218, German Auslegeschrift No. 22 37 316, and German Offenlegungsschrift No. 27 22 751.

In many cases, the pearl polymer has a tendency to adhere to form larger aggregates, which is generally undesirable from the point of view of handling. This disadvantage can be avoided if a polymer is dissolved in the monomer phase to increase its viscosity. In order not to detract from the hydrophilicity of the end product, this polymer additive should also be hydrophilic and can, for example, comprise the same monomers as the pearl polymer except for the crosslinking monomers. In case a water-methanol mixture is used as the diluent, polymethacrylamide is suitable, for example. Effective amounts of the polymer additive of this type are between 0.1 and 20 percent by weight, for example, calculated on the weight of the monomer phase. Further polymer additives which can be used are, for example, copolymers of lower alkyl acrylates, such as butyl acrylate, with acrylamide or methacrylamide or glycidyl methacrylate.

After conclusion of the pearl polymerization, the polymer pearls can be filtered off from the organic medium. If water or other compounds having active hydrogen atoms, such as alcohols or glycols, have been used as the diluent, these must be removed from the pearls since otherwise a reaction with the oxirane groups on extended storage must be feared. Volatile diluents such as water and methanol are easily removable by drying. Difficultly volatile diluents such as glycol, formamide, or dimethylsulfoxide, can be easily removed by washing them out with volatile solvents such as acetone. Subsequently, the residues of the solvent are evaporated. After drying, the polymer pearls are hard and dry and can be stored for as long as desired in the absence of atmospheric moisture.

For loading with protein, the pearls are combined with a solution of the protein of the highest possible concentration, for which purpose practically only aqueous solutions come into consideration. The most important field of use is for the immobilization of enzymes such as penicillin-acylase, trypsin, or lactase.

The following Examples, given by way of illustration, show the increase of the binding capacity by the use of a diluent combination according to the present invention (Example 1=methanol/water) in contrast to the use of only a single diluent (Example 2=formamide).

The highest binding capacity can be determined by variation of the mixing ratio of the diluent components (A) and (B) (cf. Example 9 in the series of Examples 7–10 and the Table supra in the specification). As can be seen by a comparison of the series of Examples 3–5 with Example 1, a change in the polymer composition can alter the location of the capacity maximum with respect to the mixing ratio (A):(B). From the comparison, an advantage can be recognized in the use of a high content of crosslinking monomers of 30 percent or more, particularly 50 percent or more, by weight of the monomer mixture.

As can be seen by a comparison of Examples 6 and 7, an exchange of one diluent component by another liquid, with the polymer composition remaining constant, can bring about a considerable change in activity, so that the maximum for each mixture of (A) with (B) must be independently determined.

The following Table is an overview of the Examples.

640 g of methanol,
160 g of water,
240 g of methylene-bis-methacrylamide,
30 g of allyl glycidyl ether,
30 g of glycidyl methacrylate, and
6 g of 4,4'-azobis-(4-cyanovalerianic acid)

is added at 50° C., distributed in the organic phase, and subsequently heated to boiling at 65°–70° C. Over a time period of about six hours, the methanol/water mixture is almost completely circulated out of the system. The batch is reacted for a further four hours to complete the polymerization and subsequently cooled to room temperature. The pearls formed are filtered off and dried in vacuum for 12 hours at 40° C.

The activity after loading with penicillin-acylase (described below) was 122 U/g.

Coupling with Penicillin-acylase 500 mg of pearls are incubated for 72 hours at 23° C. with 1.6 ml of a penicillin-acylase solution containing 1.05 ml of the enzyme in 0.1M potassium phosphate buffer, containing sodium acetate, at a pH of 7.5. Thereafter, the pearls are separated by filtration, washed three times with 1M sodium chloride solution, and washed twice with phosphate buffer at pH 7.5. The enzyme pearls obtained are incubated with 20 ml of 2 percent potassium-penicillin G solution in 0.05M sodium phosphate buffer (pH 7.5) at 37° C. and the phenylacetic acid liberated is titrated with 0.5M NaOH. The enzyme activity is calculated per 1 gram of moist pearls, with 1 U/g corresponding to the consumption of 1 micromol of NaOH per minute and per gram of moist pearl.

EXAMPLE 2 (COMPARISON EXAMPLE)

The apparatus and reaction procedure are the same as in Example 1 with the exception that no solvent is circulated out of the system.

| Example No. | Monomer mixture (percent by weight) | | | | Diluent (percent by weight) | | | Activity of Penicillin-acylase [or Trypsin] |
| --- | --- | --- | --- | --- | --- | --- | --- | --- |
| | | | | | Component (A) | | Component (B) | |
| | MA | MBMA | GM | AGE | Water | Formamide | Methanol | |
| 1 | — | 80 | 10 | 10 | 20 | — | 80 | 122 |
| 2 | — | 80 | 10 | 10 | — | 100 | — | 73 |
| 3 | 30 | 30 | 20 | 20 | 40 | — | 60 | 0 |
| 4 | 30 | 30 | 20 | 20 | 80 | — | 20 | 65 [6.5] |
| 5 | 30 | 30 | 20 | 20 | 90 | — | 10 | 7 |
| 6 | 10 | 50 | 20 | 20 | 70 | — | 30 | 30 |
| 7 | 10 | 50 | 20 | 20 | — | 70 | 30 | 125 |
| 8 | 10 | 50 | 20 | 20 | — | 10 | 90 | 71 |
| 9 | 10 | 50 | 20 | 20 | — | 90 | 10 | 125 |
| 10 | 10 | 50 | 20 | 20 | — | 100 | — | 95 |
| 11* | 30 | 30 | 20 | 20 | 80 | — | 20 | [10.2] |

MA = Methacrylamide
MBMA = Methylene-bis-methacrylamide
GM = Glycidyl methacrylate
AGE = Allyl-glycidyl ether
*With use of polymethacrylamide in the monomer phase

EXAMPLE 1

1740 g of n-hexane, 1100 g of perchloroethylene, 9 g of a polymeric emulsifier (a copolymer comprising 95 parts of n-butyl methacrylate and 5 parts of 2-trimethylammonium-ethyl-methacrylate-chloride), and 5 g of dry ice are introduced into a six liter stirred vessel equipped with a thermometer, water separator, reflux condenser, and nitrogen inlet tube. While stirring and introducing nitrogen, a mixture of

| | | |
| --- | --- | --- |
| Reactor Contents: (Suspending Phase) | 1740 g of | n-heptane, 1100 g of perchloroethylene, |
| | 5.6 g of | emulsifier, and 5 g of dry ice. |
| Monomer Mixture: | 1200 g of | formamide, 240 g of methyl-bis-methacrylamide, 30 g of allyl glycidyl ether, |
| | 30 g of | glycidyl methacrylate and 6 g of benzoyl peroxide. |

At the end of the reaction, the phase present over the settled pearls is decanted and the pearls are washed three times with 2000 ml of acetone and separated by filtration. The pearls were then washed three more times with acetone and dried for 12 hours in vacuum. After coupling with penicillin-acylase, an activity of 73 U/g was found.

EXAMPLE 3

The apparatus, suspending phase, and reaction procedure are analogous to Example 1. The monomer phase comprises:
  480 g of methanol,
  320 g of water,
  90 g of methacrylamide,
  90 g of methylene-bis-methacrylamide,
  60 g of allyl-glycidyl ether,
  60 g of glycidyl methacrylate, and
  6 g of 4,4'-azobis-(4-cyanovalerianic acid)
After an attempt to couple penicillin-acylase to the polymer, no enzyme activity was determined.

EXAMPLE 4

Example 3 is repeated using 160 g of methanol and 640 g of desalted water in the monomer phase. Pearls are obtained which are partially aggregated.

After coupling with penicillin-acylase, an enzyme activity of 65 U/g was found.

EXAMPLE 5

Example 3 is repeated with 80 g of methanol and 720 g of water in the monomer phase. After coupling with penicillin-acylase, an enzyme activity of 7 U/g was found.

EXAMPLE 6

The apparatus, suspending phase, and reaction procedure are analogous to those in Example 1. The monomer phase is as follows:
  240 g of methanol,
  560 g of water,
  150 g of methylene-bis-methacrylamide,
  30 g of methacrylamide,
  60 g of allyl-glycidyl ether,
  60 g of glycidyl methacrylate, and
  6 g of 4,4'-azobis-(4-cyanovalerianic acid).
After coupling with penicillin-acylase, an enzyme activity of 30 U/g was found.

EXAMPLE 7

The apparatus, suspending phase, and reaction procedure are analogous to those of Example 2. The monomer phase was as follows:
  553 g of formamide,
  237 g of methanol,
  150 g of methylene-bis-methacrylamide,
  60 g of allyl glycidyl ether,
  60 g of glycidyl methacrylate,
  30 g of methacrylamide,
  6 g of benzoyl peroxide, and
  6 g of dimethylaniline (added after the distribution of the monomer phase in the organic phase).
After coupling with penicillin-acylase, an enzyme activity of 125 U/g was found.

EXAMPLE 8

Example 7 is repeated using 79 g of formamide and 711 g of methanol in the monomer phase.

After coupling with penicillin-acylase, an enzyme activity of 71 U/g was found.

EXAMPLE 9

Example 7 is repeated using 711 g of formamide and 79 g of methanol in the monomer phase.

After coupling with penicillin-acylase, an enzyme activity of 125 U/g was found.

EXAMPLE 10 (COMPARISON EXAMPLE)

Example 7 is repeated with 791 g of formamide in the monomer phase.

After coupling with penicillin-acylase, an enzyme activity of 95 U/g was found.

EXAMPLE 11

The apparatus, suspending phase, and reaction conditions are analogous to those in Example 1.
The monomer phase comprises:
  30 g of polymethacrylamide,
  160 g of methanol,
  640 g of water,
  81 g of methacrylamide,
  81 g of N,N'-methylene-bis-methacrylamide,
  54 g of allyl-glycidyl ether,
  54 g of glycidyl methacrylate, and
  6 g of 4,4'-azobis-(4-cyanovalerianic acid).
Uniform round pearls are obtained, in contrast to the pearls obtained in Example 4.

What is claimed is:

1. A method for making a pearl-like crosslinked hydrophilic carrier polymer capable of binding proteins, which method comprises inverse pearl polymerizing, by free radical polymerization, a monomer phase distributed as droplets in a non-aqueous organic medium, said monomer phase comprising a monomer mixture of
  (1) 30 to 95 percent, by weight of the total weight of polymerizable monomers, of at least one compound selected from the group consisting of acrylamide, methacrylamide, methyl-bisacrylamide, and methylene-bis-methacrylamide,
  (2) 0 to 65 percent of further hydrophilic free radically polymerizable conomers,
  (3) 5 to 60 percent of at least one unsaturated free radically polymerizable monomer having an oxirane group, and
  (4) 0 to 25 percent of at least one other free radically polymerizable comonomer of slight hydrophilicity, of which polymerizable monomers at least 5 percent by weight are monomers having at least two polymerizable double bonds, said monomer phase further including a diluent which is a mixture of
  (A) at least one solvent selected from the group consisting of water, formamide, glycol, and dimethylsulfoxide, and
  (B) at least one organic liquid different from (A) which forms a homogeneous phase with the aforesaid monomer mixture and with (A), has a molecular weight below 200, and contains at least 20 percent by weight of oxygen, as hydroxyl groups, (A) and (B) being present in said diluent mixture in a ratio such as forms a homogeneous phase with said monomer mixture and such that the monomer phase comprising said monomer mixture and diluent mixture is incompatible with, and suspended in, said non-aqueous organic medium.

2. A method as in claim 1 wherein (B) has a total solubility parameter between 9 and 15 Hildebrand units or has a dispersive solubility parameter between 7 and 9 Hildebrand units.

3. A method as in claim 1 wherein (B) is completely miscible with water at room temperature.

4. A method as in claim 3 wherein said diluent is a mixture of water and methanol.

5. A method as in claim 1 wherein a polymer is dissolved in the monomer phase before the onset of polymerization.

6. A hydrophilic pearl polymer made by the method of claim 1.

7. A hydrophilic pearl polymer as in claim 6 having a protein bound thereto.

* * * * *